United States Patent [19]
Allen et al.

[11] Patent Number: 6,141,095
[45] Date of Patent: Oct. 31, 2000

[54] APPARATUS FOR MEASURING AND APPLYING INSTRUMENTATION CORRECTION TO PRODUCE A STANDARD RAMAN SPECTRUM

[75] Inventors: Fritz Schreyer Allen, Corrales; Jun Zhao; Danny S. Butterfield, both of Albuquerque, all of N. Mex.

[73] Assignee: New Chromex, Inc., Albuquerque, N. Mex.

[21] Appl. No.: 09/313,905

[22] Filed: May 18, 1999

Related U.S. Application Data

[60] Provisional application No. 60/088,816, Jun. 10, 1998.

[51] Int. Cl.[7] .............................. G01J 3/44; G01N 21/65
[52] U.S. Cl. ........................................................... 356/301
[58] Field of Search ............................................ 356/301

[56] References Cited

U.S. PATENT DOCUMENTS

| | | |
|---|---|---|
| 4,932,768 | 6/1990 | Gobeli et al. ............................ 350/611 |
| 5,194,847 | 3/1993 | Taylor et al. ............................ 340/557 |
| 5,243,546 | 9/1993 | Maggard ............................ 364/571.02 |
| 5,455,673 | 10/1995 | Alsmeyer et al. ....................... 356/301 |
| 5,553,616 | 9/1996 | Ham et al. ............................... 128/633 |
| 5,596,196 | 1/1997 | Cooper et al. ....................... 250/339.12 |
| 5,610,836 | 3/1997 | Alsmeyer et al. ....................... 364/498 |
| 5,652,653 | 7/1997 | Alsmeyer et al. ....................... 356/301 |
| 5,657,404 | 8/1997 | Buchanan et al. ......................... 385/12 |

*Primary Examiner*—F. L. Evans
*Attorney, Agent, or Firm*—Ray R. Regan

[57] ABSTRACT

An apparatus for measuring and applying instrumentation correction to produce a standard Raman spectrum of a sample to be analyzed. A source of incident radiation is included. Also included are means for providing from the incident radiation an incident beam and a monitor beam. The incident beam is directed at the sample. The invention includes means for generating from the sample a Raman beam. Spectral data may be collected directly from the monitor beam and the Raman beam. Spectral data may be collected substantially simultaneously from the monitor beam and the Raman beam, or sequentially. One or more integral transforms are applied to spectral data to produce the standard Raman spectrum of the sample.

45 Claims, 4 Drawing Sheets

6,141,095

APPARATUS FOR MEASURING AND APPLYING INSTRUMENTATION CORRECTION TO PRODUCE A STANDARD RAMAN SPECTRUM

CROSS-REFERENCE TO RELATED APPLICATION

As provided in 35 U.S.C. §119, applicants claim priority to this nonprovisional patent application based on the copending provisional United States patent application filed by the co-inventors named herein, filed in the United States Patent and Trademark Office on Jun. 10, 1998, Serial or Application No. 60/088,816. No new matter has been added to the nonprovisional application.

FEDERALLY SPONSORED RESEARCH AND DEVELOPMENT

None.

FIELD OF THE INVENTION

The present invention pertains generally to the field of spectroscopy. More particularly, the present invention pertains to an apparatus and method for applying instrumentation correction to achieve a standard Raman spectrum. The present invention is particularly, but not exclusively, useful for providing an apparatus and method for achieving superior precision and accuracy in connection with Raman spectra, as well as instrument independence, while eliminating the need for ideal excitation frequency stability.

BACKGROUND OF THE INVENTION

Spectroscopy is a general term for the process of measuring energy or intensity as a function of wavelength in a beam of light or radiation. Many conventional spectroscopes, and components comprising a spectroscope system, also referred to as an instrument, may include basic features and components such as a slit and a collimator for producing a parallel beam of radiation, one or more prisms or gratings for dispersing radiation through differing angles of deviation based on wavelength, and apparatus for viewing dispersed radiation. Spectroscopy uses absorption, emission, or scattering of electromagnetic radiation by atoms, molecules or ions to qualitatively and quantitatively study physical properties and processes of matter.

Light or radiation directed at a target, or sample, during operation of a spectroscope system may be referred to as incident radiation. Redirection of incident radiation following contact with a sample of physical matter ("sample") commonly is referred to as scattering of radiation. To the extent that atoms or molecules in a sample absorb all or a portion of incident radiation, rather than reflect incident radiation, a sample may become excited, and the energy level of the sample may be increased to a higher energy level. Electromagnetic radiation, including incident radiation, that passes through a sample may produce a small portion of light that is scattered in a variety of directions. Light that is scattered but continues to have the same wavelength as the incident radiation may also have the same energy, a condition often referred to as Rayleigh or elastically scattered light. Incident radiation that is scattered during a change of vibrational state in molecules may be scattered with a different energy, and such scattered light may be called Raman scattered light. Such phenomena have been used in conjunction with spectroscopy to qualitatively and quantitatively study physical properties and processes, including identification of chemical properties, compositions, and structures of a sample.

A wave associated with electromagnetic radiation may be described by wavelength, the physical length of one complete oscillation, and by frequency of the wave, the number of oscillations per second that pass a point. If incident radiation is directed at a sample, the wavelength of the incident radiation ("incident wavelength") may remain substantially unchanged in scattered radiation. Alternatively, if incident radiation is directed at a sample, the wavelength in the scattered radiation may acquire one or more different wavelengths than the incident wavelength. The energy differential between the incident radiation and the scattered radiation may be referred to as a Raman shift. Spectroscopic measurement of Raman scattered light seeks to measure the resulting wavelength of such scattered light.

Raman scattered light may occur at wavelengths shifted from the incident light by quanta of molecular vibrations. The phenomenon of Raman scattered light, therefore, is useful in spectroscopy applications for studying qualities and quantities of physical properties and processes, including identification of chemical properties, compositions, and structure in a sample. Currently, Raman shift spectroscopic analytical techniques are used for qualitative and quantitative studies of samples. If incident radiation is used to scatter light from a sample, and scattered radiation data is measured, the scattered radiation may provide one or more frequencies associated with the sample, as well as the intensities of those shifted frequencies. The frequencies may be used to identify the chemical composition of a sample. If, for example, intensities are plotted on a Y-axis, and frequency or frequencies are plotted on an X-axis, the frequency or frequencies may be expressed as a wave number, the reciprocal of the wavelength expressed in centimeters. The X-axis, showing frequency or frequencies, may be converted to a Raman shift in wave numbers, the measure of the difference between the observed wave number position of spectral bands, and the wave number of radiation appearing in the incident radiation.

While these principles and phenomena are known, efforts to apply the principles and phenomena to qualitative and quantitative analyses of samples has not resulted in uniform, predictable results, or in acceptable levels of precision and accuracy of Raman spectra. Because of instrumentation variabilities, inherent weakness of a Raman scattered signal, fluorescence, and other limitations associated with spectroscopy instruments, the goal of producing a standard Raman spectrum for use in sample analyses has proven to be a challenge not achieved by apparatus and methods known in the art.

For example, spectroscopic measurements of Raman scattered light seeking to measure wavelength or intensities, or both, of scattered light, may be affected by the instrument, or spectroscopic system, itself. A number of components of an instrument may contribute individually and collectively to undesirable instrumentation variabilities that affect spectral data measured by the instrument. Thus, Raman scattered radiation from a sample may be observed, measured, and directed through an instrument by optics of a spectrometer, may be coded by a device such as an interferometer, and may be directed to one or more detectors to record Raman spectra. Any one, or all, of such components of a spectrometer system may induce or contribute to instrumentation variabilities that may reduce or adversely affect the precision and accuracy of measurements of Raman scattered light.

Further, Raman scattering is a comparatively weak effect when compared with Rayleigh or elastic scattering.

Nevertheless, Raman scattering offers a significant opportunity for qualitative and quantitative studies of physical properties and processes, including identification of chemical compositions and structure in samples of physical matter. To appreciate these phenomena, as well as understand the problems solved by the present invention, it should be noted that depending on the compound comprising a sample, only about one scattered photon in $10^{6-8}$ tends to be Raman shifted. Because Raman scattering, therefore, is such a comparatively weak phenomenon, a spectrometer used to disperse radiation for measurement purposes should have minimal stray light and be able to substantially reject Rayleigh scattering. Otherwise, a Raman shift may not be measurable. In addition, because multiple lines in the frequency of the source of incident radiation may cause shifted, multiple sets of spectra from a sample, conventional Raman experimentation discloses that a source or sources of incident radiation that causes excitation in a sample used in connection with a spectrograph should be substantially monochromatic, preferably providing a single frequency or wavelength. Recognition that the source of incident radiation requires a substantially monochromatic frequency has led to use of a variety of laser light sources as a source of incident radiation because of the substantially monochromatic frequency and high intensity of a laser. Gas lasers such as helium—neon, helium—cadmium, argon-ion, krypton-ion, as well as solid state lasers including Nd-YAG, and diode lasers, solid state tunable lasers, liquid dye lasers, and other lasers, have been used in spectroscopy apparatus seeking to measure Raman spectral data, including wavelength.

Preferably, a source of incident radiation would provide a substantially monochromatic frequency and radiation closer to the blue portion of the visible light spectrum providing short wavelength excitation because the Raman effect is enhanced by use of short wavelength excitation, and because of the enhanced quantum efficiency ("QE") of charged coupled detectors ("CCD's") in use today. Indeed, an undesirable result of incident radiation on a sample occurs if a sample generates red shifted radiation as part of a radiation absorption process, a phenomenon commonly referred to as fluorescence. Fluorescence occurs when absorbed radiation is lowered in frequency by internal molecular processes and emitted as radiation that is closer to the red end of the visible light spectrum. Fluorescence sometimes may be strong enough in comparison with the Raman shift to swamp, or substantially eliminate, the weaker Raman signal. Current technology, however, particularly in connection with silicon detectors, substantially restricts use of instrument components that tend to provide radiation far into the infrared ("IR") region of the light spectrum, rather than blue.

Instrumentation variabilities, however, are not the only limiting factors affecting current Raman spectroscopy analyses. While a laser often is suitable as a source of incident radiation, the frequency or frequencies associated with incident radiation from a laser may be unstable. Unstable frequencies of incident radiation are yet other variations that may affect measurements of a Raman signal. While lasers may provide a substantially monochromatic source of incident radiation, variations in the center wavelength and frequency of lasers, even those that are apparently similar, also may occur. To the extent that wavelengths of a source of incident radiation vary, the resultant Raman spectra may vary. Current commercial applications of Raman principles and phenomena are hindered by requirements for substantially constant monitoring of excitation wavelengths from the source of incident radiation to avoid erroneous data.

Proposals for overcoming this limitation have included, therefore, use of two or more sources of frequency stabilized incident radiation, one as the primary or actual source, a second as a reserve or backup source. Use of two or more sources of frequency stabilized incident radiation, however, adds significantly to the costs of such a system. Use of an actual source of frequency stabilized incident radiation, with a reserve source of frequency stabilized incident radiation as a backup, resolves neither possible failure of both sources of incident radiation, nor undesirable variations of wavelength in both excitation sources. Costs associated with providing two or more sources of frequency stabilized incident radiation in an apparatus that employs only one source of frequency stabilized incident radiation also is comparatively high.

In addition, current spectrometer systems seeking to use a Raman shift in connection with qualitative or quantitative analyses of a sample may have to overcome limited sensitivity of one or more instrument detectors currently available for use in spectrometer systems. For example, a detector consisting of a silicon charge coupled device has a limited range of sensitivity in detecting wavelength. A practical upper wavelength for silicon charge coupled devices currently available is about 1.15 microns. Current detector sensitivity to wavelength is not constant from upper to lower limits. Detectors that appear to be similar may exhibit different sensitivity responses. Further, charge coupled detectors may have multi-channel capabilities, allowing a detector to accept spectra substantially simultaneously, or substantially at one point in time ("real time"). Some detectors, however, are capable of collecting information only over time, rather than in real time. The need for a detector to accept spectra substantially simultaneously, or at one point in time, is due in part to system drift that may be associated with the spectroscopy system itself, as well as with time differences occurring during data gathering.

Thus, present spectrometer technology indicates problems and limitations caused by spectrometry hardware components. The spectroscopic instrument may exhibit differences among similar or related components, or instrumentation variabilities, that may induce or cause differences in measurements of spectra from the same sample. As described, differences in measurements of spectra from the same sample may be caused by instrumentation variabilities including optics, detectors, and other components of a spectroscopy system. Efforts have been made to control the effect of instrumentation variabilities on qualitative and quantitative analyses performed using the Raman shift, but none has proven consistently successful. Further, none of the efforts has resulted in a cost effective spectroscopy system for measuring a Raman shift that achieves superior precision and accuracy in connection with Raman spectra, as well as instrument independence that results in a fully automated system.

For example, at least one system proposes use of a sample and a secondary reference material from which a spectrograph may gather intensity and wavelength information of and from an excitation source. Introduction of one or more secondary reference materials adds considerable complexity to an application of the Raman shift principles. The spectrum of a reference material must be known, and must remain constant during use. A reference material, however, may not provide consistent measurements because of variations in the reference material. Requiring use of a secondary reference material also results in loss of resolution in the sample because, for example, any Raman spectra of a sample may be broadened by spectral properties of the reference material. Significant broadening of a Raman spectrum will yield an inaccurate qualitative or quantitative analysis of a sample. Also, because significant portions of signals associated with sources of incident radiation may be used to obtain a spectrum or spectra of a reference material, the relationship between the signal and the noise shown in graphical readings portraying the data is reduced.

There are, therefore, a number of problems to solve to achieve the goal of providing an apparatus for measuring and applying instrumentation correction to produce a standard Raman spectrum that permits a user to make spectroscopic measurements using principles associated with Raman scattered light. The problems to be solved include providing an apparatus for measuring and applying instrumentation correction to produce a standard Raman spectrum. Another problem includes providing an apparatus that produces and achieves superior precision and accuracy in connection with measurements of Raman spectra, as well as instrument independence, and achieving such results by providing a fully automated system. The term "fully automated system" means a system that includes the capability of not requiring an operator of the system to be either skilled in the art or have special skills, yet is capable of maintaining the quality of the data over a time period unmonitored or unattended by an operator of the system. In addition, what should be achieved is high resolution Raman spectra using an apparatus and method of operation of the apparatus that is easy to use, predictably accurate, easy to practice, and relatively cost effective.

What is needed, therefore, is an apparatus for measuring and applying instrumentation correction to produce a standard Raman spectrum ("Raman apparatus"). The Raman apparatus should be capable of providing and achieving superior precision and accuracy in connection with Raman spectra. Also needed is a Raman apparatus that is instrument independent, while eliminating the need for ideal excitation frequency stability. Such a Raman apparatus also should be capable of producing a high resolution Raman spectrum unaffected by Rayleigh or other undesirable radiation scattering. Wavelengths and intensities should be determinable substantially simultaneously, in real time. The Raman apparatus should be able to provide from the source of incident radiation at least an incident beam and a monitor beam for purposes of analyzing incident radiation. The Raman apparatus also should provide high resolution of monitor beam measurements and data, using, as a nonexclusive example, one or more higher resolution dispersive optics such as one or more prisms or gratings. Also needed in the Raman apparatus is a detector or detectors capable of collecting spectral information as a whole, in real time, rather than over a time differential. Effects of instrumentation variabilities on the Raman spectra caused by characteristics of components of the Raman apparatus itself, should be compensated for. The Raman apparatus should provide a fully automated system, meaning that any variations in a source of incident radiation are determined and resolved in real time. The Raman apparatus also should not require use of a significant portion of the source of incident radiation in the process of determining characteristics of the source of incident radiation.

One of many advantages of the present invention, therefore, is a Raman apparatus for measuring and applying instrumentation correction to produce a standard Raman spectrum. An additional advantage of the present invention is a Raman apparatus that provides standard reference data from any spectrometer or similar instrument because instrumentation variabilities are rendered irrelevant. The present invention is capable also of achieving superior precision and accuracy in connection with Raman spectra, as well as instrument independence, while eliminating the need for ideal excitation frequency stability. The present invention, therefore, is capable of achieving superior precision and accuracy, while being independent of intensity fluctuations in connection with the source of incident radiation, and of frequency drifts in the source of incident radiation, as well as in the system itself. As indicated, the present invention also provides a system that is capable of being fully automated.

Another advantage of the present invention is the ability of the Raman apparatus to provide double dispersion of a monitor beam to acquire substantially simultaneously high resolution spectral data about a source of incident radiation and instrumentation variabilities. The present invention substantially simultaneously collects spectral data from a monitor beam and from a Raman beam, which originated from a sample and from a source of incident radiation, in terms of both spectral properties and intensity levels. It provides a detector having optimum detector sensitivity capable of accepting one or more dispersions, including double dispersion of a monitor beam, that enables the detector to collect spectral information as a whole, in real time, rather than over a time differential. The Raman apparatus also compensates for, or obviates, effects on Raman spectra caused by characteristics of components of the Raman apparatus itself. Use of one or more reference materials to obtain or generate data is not required. Another advantage of the present invention is its ability to enlarge the universe of both users and applications because of the several advantages of the present invention, including the fact that the apparatus and method of operation of the present invention respectively are easy to use and to practice, and cost effective for their intended purposes.

These advantages and other features of an apparatus for measuring and applying instrumentation correction to produce a standard Raman spectrum will become apparent to those skilled in the art when read in conjunction with the accompanying following description, drawing figures, and appended claims.

SUMMARY OF THE INVENTION

An apparatus for measuring and applying instrumentation correction to produce a standard Raman spectrum of a sample, according to the present invention, includes a source of incident radiation. The source of incident radiation provides substantially monochromatic radiation or light. A source of incident radiation, therefore, may include a laser. A variety of laser light sources may be used in connection with the present invention not only because of the substantially monochromatic nature of the radiation, but also because of the high intensity of laser radiation.

An apparatus for measuring and applying instrumentation correction to produce a standard Raman spectrum of a sample also includes one or more means for providing from the incident radiation an incident beam and a monitor beam. A means for providing an incident beam and a monitor beam is installation of one or more wave guides, such as a beam splitter waveguide, in the path of the incident radiation. The incident beam is directed at the sample to be analyzed. The incident beam induces or generates scattered radiation on contact with the sample. The scattered radiation has an energy differential different from, and one or more wavelengths different than, the incident radiation, comprising the Raman shift. For convenience, the Raman shift is described in this document as a Raman beam to be analyzed by the instrument.

The incident beam and the Raman beam may pass through a variety of instrumentation components during operation of the instrument. The arrangement and combination of instrument structural components, however, provided in connection with the present invention, are not determinative of the capability of the present invention to achieve superior precision and accuracy in connection with the measurement of a standard Raman spectrum, instrument independence, and elimination of the need for ideal excitation frequency stability. Thus, the Raman beam and incident beam may be directed to one or more wave guides, optics, reflectors, mirrors, focusing lenses and filters. The present invention may also include one or more sources of white light for imparting instrument response or shape correction to the Raman beam, as well as means for adding a frequency calibration standard to the instrument. Likewise, the present invention may include a variety of instrumentation components for collecting monitor beam spectral data. As is true of the Raman beam, the precise arrangement and combination of structural components is not determinative of the ability of the present invention to achieve superior precision and accuracy in connection with the measurement of a standard Raman spectrum, as well as instrument independence, while eliminating the need for ideal excitation frequency stability. The monitor beam, for example, may be directed from a waveguide through one or more devices for imparting to the monitor beam a frequency calibration.

The Raman beam and monitor beam also are directed to one or more detectors. The one or more detectors contribute to collecting and displaying the spectral data of the incident wavelength of the monitor beam, and in determining intensity of the monitor beam, substantially simultaneously with establishment of the Raman radiation from the incident beam. To achieve the superior precision and accuracy of Raman spectra resulting from the present invention, however, a number of different means may be used. The monitor beam may be measured in any number of ways, and at any number of points, after the incident radiation is divided into a incident beam and a monitor beam. The instrumentation components may be arranged in the instrument to achieve collection of spectral data substantially simultaneously from the monitor beam and the Raman beam.

The present invention also includes means for applying one or more integral transforms to the Raman beam and to the monitor beam spectral data thus collected. In the preferred embodiment of the present invention, the means for applying the one or more integral transforms is a computer. Equations for deconvolution are well known. As applied to the present invention, the equations may be applied to spectral data to remove the effect of an impulse function on a response function, thus removing undesirable frequency wanderings and intensities from the spectral data. Frequency measurements associated with raw Raman spectral data may thus be transformed. Accordingly, as disclosed in this document, an integral transform refers to one or more calculations and processes by which the present invention compensates for undesirable Raman effects that are attributable to the less than ideal characteristics of the source of incident radiation, including frequency and intensity instability. The present invention thus adjusts for shifts, or multiple lines, that may appear in measurements of the incident radiation, and shifts, or variations, in the spectrum or spectra of a sample being analyzed by a spectrometer system. An integral transform, according to the present invention, may also include methods and calculations associated with autocorrelation. Substantially simultaneous spectral data collection in connection with integral transforms, in conjunction with the components of the apparatus, combine to provide high resolution Raman spectra that are not dependent on frequency stability in the source of incident radiation, and are independent of intensity fluctuations associated with the source of incident radiation. In addition, substantially simultaneous data measurements also allows user interchangeability of sample spectra among a number of spectrometers and similar apparatus because instrument variabilities are rendered irrelevant. Also, because corrections may be applied to correct for instrument variabilities, one or more multi-mode lasers that are not mode stabilized may be used as a source of incident radiation. As an additional result, more applications of the Raman principles are made possible, because a standard Raman spectrum is provided.

The foregoing has outlined broadly the more important features of the invention to better understand the detailed description which follows, and to better understand the contribution of the present invention to the art. Before explaining at least one embodiment of the invention in detail, it is to be understood that the invention is not limited in application to the details of construction, and to the arrangements of the components, provided in the following description or drawing figures. The invention is capable of other embodiments, and of being practiced and carried out in various ways. Also, the phraseology and terminology employed in this disclosure are for purpose of description, and should not be regarded as limiting.

As those skilled in the art will appreciate, the conception on which this disclosure is based readily may be used as a basis for designing other structures, methods, and systems for carrying out the purposes of the present invention. The claims, therefore, include such equivalent constructions to the extent the equivalent constructions do not depart from the spirit and scope of the present invention. The abstract associated with this disclosure is neither intended to define the invention, which is measured by the claims, nor intended to be limiting as to the scope of the invention in any way.

The novel features of this invention, and the invention itself, both as to structure and operation, are best understood from the accompanying drawing, considered in connection with the accompanying description of the drawing, in which similar reference characters refer to similar parts, and in which:

DESCRIPTION OF THE PREFERRED EMBODIMENTS

Figure 1:
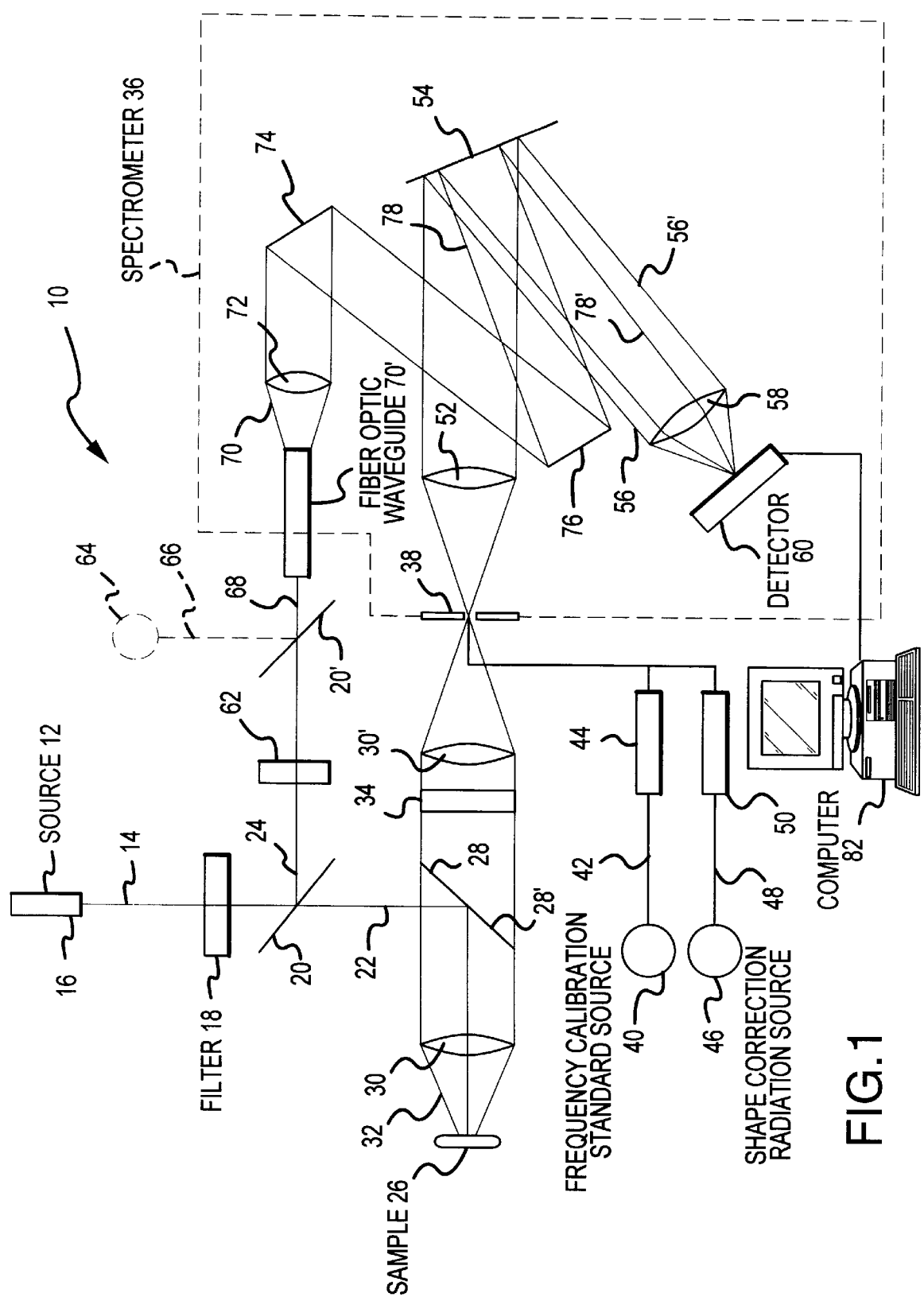
FIG. 1 is a schematic drawing of an apparatus for measuring and applying instrumentation correction to produce a standard Raman spectrum of a sample according to the present invention.

Referring initially to FIG. 1, an apparatus for measuring and applying instrumentation correction to produce a standard Raman spectrum is shown schematically, and generally designated 10. As also shown, an apparatus for measuring and applying instrumentation correction to produce a standard Raman spectrum 10 includes a source 12 of incident radiation 14. Source 12 of incident radiation 14 provides incident radiation 14 in the form of a substantially monochromatic radiation or light. Source 12 of incident radiation 14, therefore, may be a laser 16. A variety of laser light sources may be used as laser 16 in connection with the present invention not only because of the substantially monochromatic nature of the radiation, but also because of the high intensity of laser radiation. Gas lasers such as helium—neon, helium—cadmium, argon-ion, krypton-ion, as well as solid state lasers such as Nd-YAG, and diode lasers, solid state tunable lasers, liquid dye lasers, and other lasers are suitable for use in connection with the present invention for measuring and applying instrumentation correction to produce a standard Raman spectrum of a target or sample. In a preferred embodiment of the present invention, laser 16 is a diode laser that has not been frequency stabilized. Laser 16 also may include multi-mode characteristics. In an alternative embodiment of the present invention, source 12 of incident radiation 14 may be a single mode laser that is frequency stable, not a diode laser. In yet another embodiment, source 12 of incident radiation 14 may be a source 12 that is not a laser 16.

As also shown in FIG. 1, the present invention includes a filter 18. In the preferred embodiment of the present invention, filter 18 is a band-pass filter for narrowing wavelengths of incident radiation 14, and for removing undesirable radiation from incident radiation 14. The arrangement and combination of instrument structural components, however, provided in connection with the present invention, is not determinative of the capability of the present invention to achieve superior precision and accuracy in connection with the measurement of a standard Raman spectrum, instrument independence, and elimination of the need for ideal excitation frequency stability. Thus, for example, the present invention also includes a waveguide 20 for providing from incident radiation 14 an incident beam 22 and a monitor beam 24 to enable the present invention to direct incident beam 22 at a sample 26 to be analyzed. Filter 18 may be located in the path of incident radiation 14 anywhere in the instrument before sample 26. And, although in a preferred embodiment waveguide 20 is a beam-splitter waveguide, a different waveguide 20 may be used in an alternative embodiment depending on the sensitivity of the instrument and the intensity of source 12 of incident radiation 14. Waveguide 20 also may include one or more prisms, partially silvered mirrors, and plate type beam splitters.

As stated, and as shown in FIG. 1, an apparatus for measuring and applying instrumentation correction to produce a standard Raman spectrum of sample 26 also includes a waveguide 20 for providing from incident radiation 14 an incident beam 22 and a monitor beam 24 to enable the present invention to direct incident beam 22 at a sample 26 to be analyzed. In a preferred embodiment of the present invention, monitor beam 24 represents a substantially smaller percentage of incident radiation 14 as compared with incident beam 22. In a preferred embodiment of the present invention, monitor beam 24 includes approximately one percent (1%) of incident radiation 14, and incident beam 22 includes the balance of incident radiation 14. The approximate ratio of 1:99 between radiation included, respectively, in monitor beam 24 and incident beam 22 is not, however, a limitation of the present invention. Different ratios may be determined and applied in connection with the practice of the present invention, depending, in part, on sensitivity of the instrument used to gather spectral data, and the wavelength and intensity of source of incident radiation 14.

The present invention also includes, as shown in FIG. 1, means for directing incident beam 22 at sample 26. Incident beam 22 may be directed at sample 26 without any intervening instrument components being located in the path of incident beam 22. The arrangement and combination of structural components provided in connection with the present invention is not determinative of the ability of the present invention to achieve superior precision and accuracy in connection with measurement of a standard Raman spectrum, as well as instrument independence, while eliminating the need for ideal excitation frequency stability. For example, incident beam 22 may be directed at a mirror 28. In a preferred embodiment of the present invention, mirror 28 is a dichroic mirror 28'. However, in an alternative embodiment of the present invention, an holographic transmissive element, or a mirror formed with a hole in the mirror may be used instead of dichroic mirror 28'. Thereafter, incident beam 22 may be directed through a lens 30. In a preferred embodiment of the present invention, lens 30 is a focusing lens in the path of incident beam 22 before incident beam 22 contacts sample 26. In an alternative embodiment of the present invention, more than one lens 30 may be located in the path of incident beam 22 before incident beam 22 contacts sample 26.

Figure 1A:
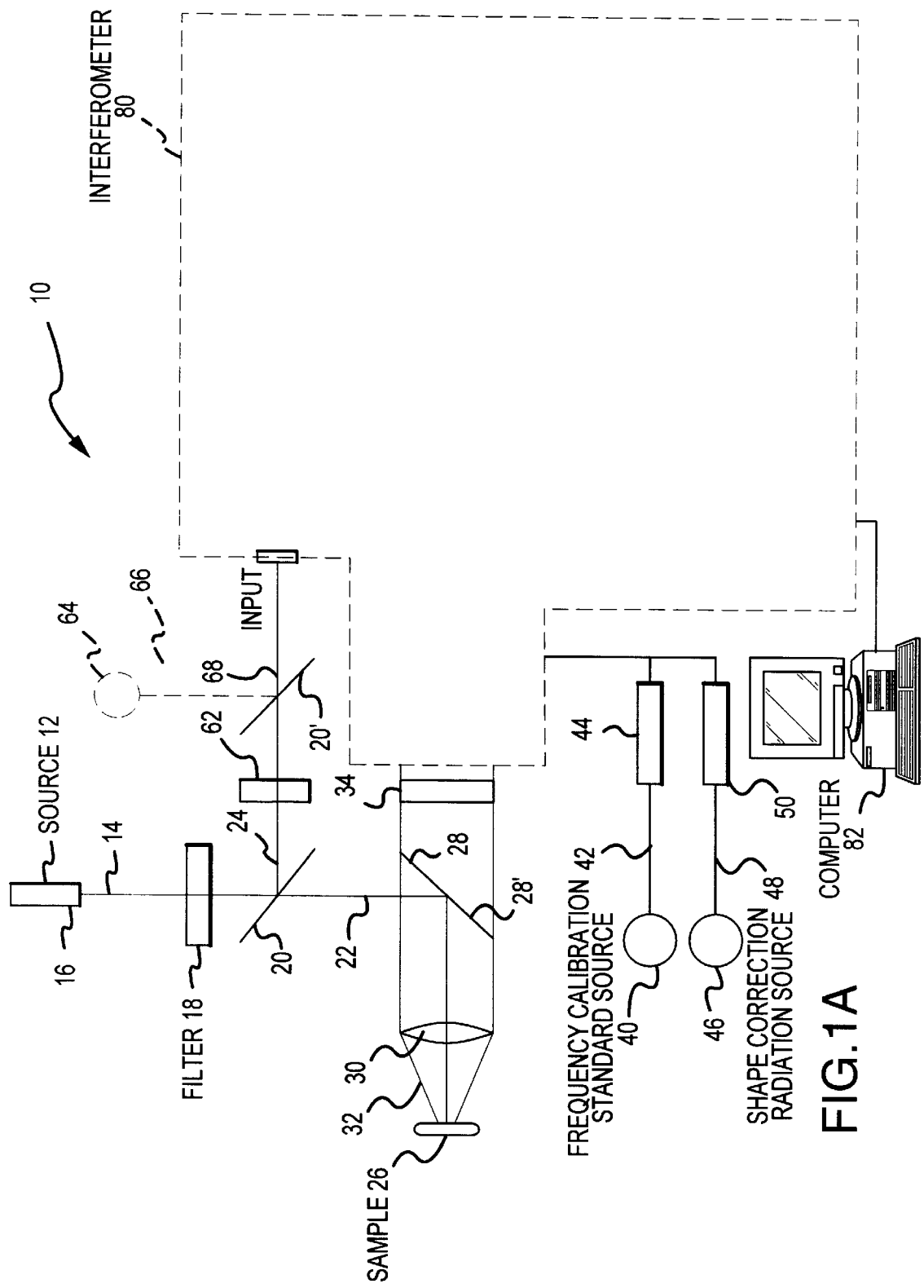
FIG. 1A is a schematic drawing of an alternative embodiment of the present invention showing use of an interferometer.

As also shown by reference to FIG. 1, incident beam 22 induces or generates on contact with sample 26 scattered radiation having an energy differential different from, and one or more wavelengths different than, incident radiation 14, or the Raman shift that, for convenience, is described in this document as a Raman beam 32. As stated, and as shown in FIG. 1, in a preferred embodiment of the present invention, a mirror 28, preferably a dichroic mirror 28', is provided. Raman beam 32 is directed back through lens 30 and dichroic mirror 28' in a 180 degree back-scatter geometry. Neither incident beam 22 nor Raman beam 32 need be co-linear. In the preferred embodiment of the present invention, however, Raman beam 32 passes back through dichroic mirror 28', then through a filter element 34, and then through a lens 30', preferably a focusing lens. Filter element 34 is, in the preferred embodiment, a long-pass filter. In an alternative embodiment of the present invention, filter element 34 is a notch filter, or any other filter that is capable of rejecting elastically scattered radiation. Raman beam 32 is, as shown in FIG. 1, positioned to enter spectrometer 36 (shown by dashed lines) through slit 38. As previously stated, however, Raman scattered radiation from a sample, such as sample 26, may be coded by a device such as an interferometer. In an alternative embodiment of the present invention, therefore, Raman beam 32 is, as shown in FIG. 1A, is positioned to enter an interferometer 80 as shown in FIG. 1A.

The present invention also includes one or more means for imparting a frequency calibration standard to the instrument and for imparting shape correction to Raman beam 32. In a preferred embodiment of the present invention, a frequency calibration standard source 40 provides a frequency calibration beam 42. Frequency calibration beam 42 is directed into spectrometer 36 using a first fiber optic waveguide 44. Frequency calibration beam 42, preferably a neon light source, may be introduced into the instrument at slit 38 of spectrometer 36, where Raman beam 32 also enters spectrometer 36. Frequency calibration provided by frequency calibration source 40 contributes to compensation for instrumentation variabilities because spectral data of a known standard may be compared with spectral data of Raman beam 32. The present invention also includes a shape correction radiation source 46 that provides a shape correction beam 48. Shape correction radiation source 46 is, in the preferred embodiment of the present invention, a white light source. In an alternative embodiment of the present invention, shape correction radiation source 46 may be a broad band fluorescent or phosphorescent source. Shape correction beam 48 is directed into spectrometer 36 using a second fiber optic waveguide 50. Shape correction beam 48 may be introduced into the instrument at slit 38 of spectrometer 36, where Raman beam 32 also enters spectrometer 36.

Referring again to FIG. 1, and to the positioning of Raman beam 32 at the entrance to spectrometer 36 at slit 38, the present invention also includes a second lens 52 located within spectrometer 36. In a preferred embodiment of the present invention, second lens 52 is a focusing lens for focusing Raman beam 32 toward a first dispersive grating 54. First dispersive grating 54 separates wavelengths of Raman beam 32 to form a dispersed signal shown diagrammatically by lines 56 and 56' in FIG. 1. Also included in the present invention is a third lens 58 for focusing dispersed signal 56-56' on detector 60. In a preferred embodiment of the present invention, detector 60 is a charge coupled device. Also in a preferred embodiment of the present invention, detector 60 is capable of displaying on one or more pixel configurations on the same detector 60 data that is associated with frequency calibration beam 42 from frequency calibration standard source 40. Detector 60 also is capable of displaying on one or more pixel configurations on detector 60 data associated with shape correction beam 48 for determining the extent, if any, spectral data is affected by instrumentation variabilities. The same detector 60 also may display the monitor beam on a separate set of pixels or spatial channel. In an alternative embodiment of the present invention, detector 60 may be a multi-channel array detector, including as a nonexclusive example a photodiode array detector. In addition, the data may be viewed on one or more detectors 60, and a second spectrometer may be provided to view monitor beam 24.

As stated, an apparatus for measuring and applying instrumentation correction to produce a standard Raman spectrum of a sample 10 also includes, as shown in FIG. 1, means for collecting spectral data substantially simultaneously from monitor beam 24 as well as from Raman beam 32. Monitor beam 24 is used to ascertain wavelength spectra and intensity of incident radiation 14. Wavelength spectra and intensity of incident radiation 14, according to the present invention, is collected substantially simultaneously with collection of spectral data in connection with Raman beam 32. Means for collecting spectral data substantially simultaneously from monitor beam 24 include a second filter 62 located in the path of monitor beam 24. In a preferred embodiment of the present invention, second filter 62 is an intensity filter. Second filter 62 is located in the path of monitor beam 24 to contribute to reduction of the intensity of source 12 of incident radiation 14. In an alternative embodiment of the present invention second filter 62 may be a diffuser. In another alternative embodiment of the present invention second filter 62 may be eliminated if detector 60 will not be so saturated as to affect deconvolution of the spectral data. Also shown diagrammatically is frequency calibration standard source 40 as second frequency calibration standard source 64. In a preferred embodiment of the present invention, second frequency calibration standard source 64 is a neon light source. In an alternative embodiment of the present invention, second frequency calibration standard source 64 may be an emitter having a stable frequency. Preferably, second frequency calibration standard source 64 provides a known wavelength or spectral data to contribute to comparing the wavelength of source 12 of incident radiation 14 with any shifts in source 12 of incident radiation 14. Second frequency calibration standard source 64 produces a second frequency calibration standard beam 66. Second frequency calibration standard beam 66 from second frequency calibration standard source 64 may be applied to monitor beam 24 at waveguide 20' located in the path of second frequency calibration standard beam 66 and in the path of monitor beam 24, as shown in FIG. 1. Second frequency calibration standard beam 66 may be superimposed on the same path as monitor beam 24. On application of a frequency calibration standard to monitor beam 24, the resulting combined monitor-calibration beam 68 results. The present invention also provides for a third waveguide 70 located in the path of combined monitor-calibration beam 68. In a preferred embodiment of the present invention, third waveguide 70 is a fiber optic waveguide 70'. Fiber optic waveguide 70' includes a fourth lens 72. Combined monitor-calibration beam 68 passes through fourth lens 72 to a turning mirror 74 that directs combined monitor-calibration beam 68 to a second dispersive grating 76, as shown in FIG. 1. Second dispersive grating 76 separates combined monitor-calibration beam 68 into different wavelengths, and provides added spectral resolution to combined monitor-calibration beam 68 before directing the resulting signal 78 and 78' to first dispersive grating 54 to be focused on detector 60. In an alternative embodiment of the present invention, dispersive grating 76 may be one or more prisms or holographic gratings. The type of dispersive grating is not a limitation of the present invention.

Figure 2:
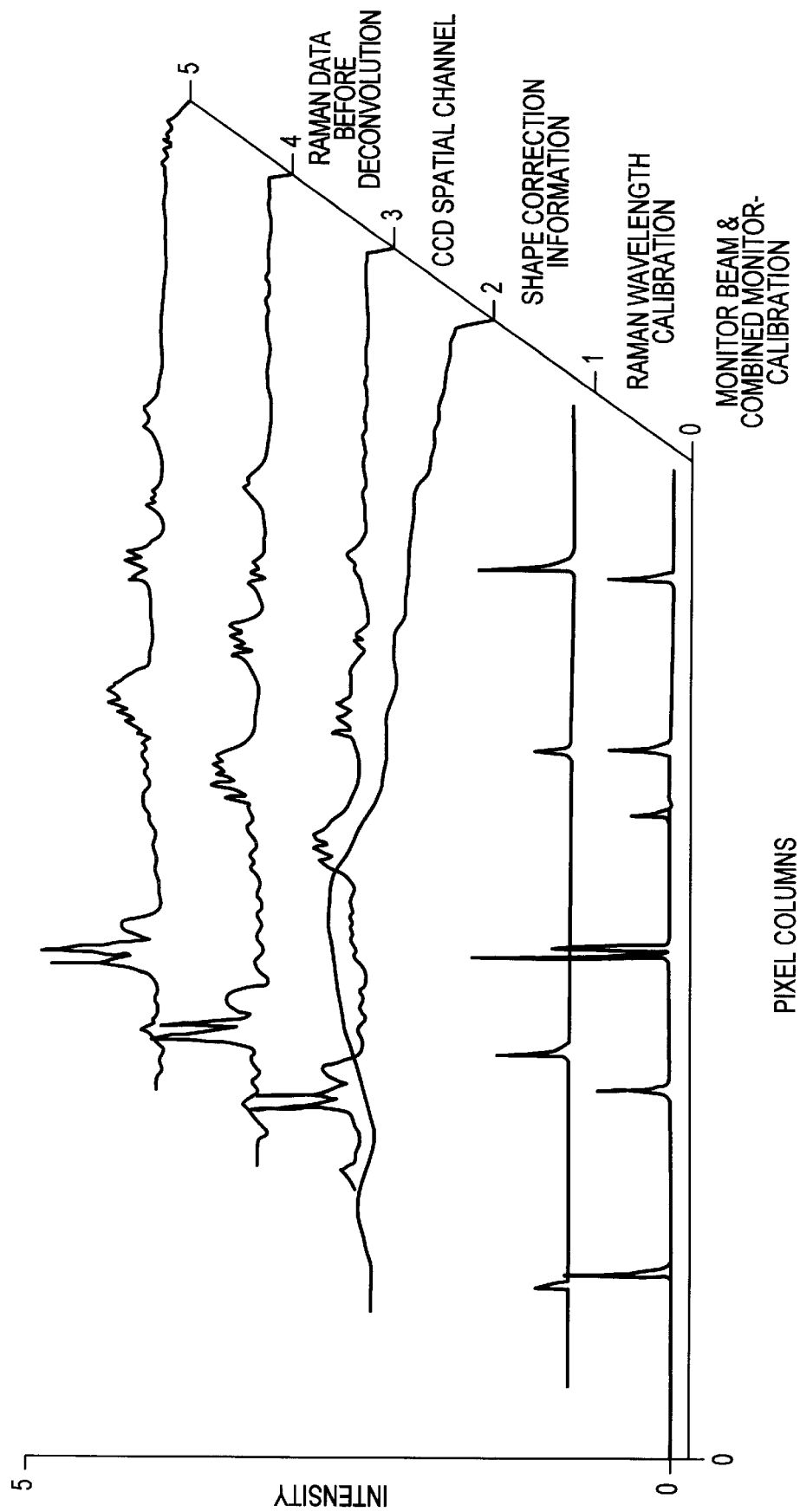
FIG. 2 is a graph showing an array of spectral data from a source of incident radiation.

The present invention also includes means for applying one or more integral transforms to Raman beam 32 and to monitor beam 24 spectral data thus collected, as shown by cross-reference among FIGS. 2–5. In the preferred embodiment of the present invention, the means for applying the one or more integral transforms is a computer 82 as shown in FIG. 1. Equations for deconvolution are well known. As applied to the present invention, the equations may be applied to spectral data to remove the effect of an impulse function on a response function, thus removing undesirable frequency wanderings and intensities from the spectral data. Frequency measurements associated with raw Raman spectral data may thus be transformed. Accordingly, as disclosed in this document, an integral transform refers to one or more calculations and processes by which the present invention compensates for undesirable Raman effects that are attributable to the less than ideal characteristics of source 12 of incident radiation 14, including frequency and intensity instability. The present invention thus adjusts for shifts, or multiple lines, that may appear in measurements of incident radiation 14, and shifts, or variations, in the spectrum or spectra of a sample 26 being analyzed by spectrometer 36 or by an interferometer (not shown). Deconvolution contributes to, but is not limited to, removal of unwanted frequency shifts and unwanted intensity changes of incident radiation 14. Autocorrelation methods, that may alternatively be applied to the Raman spectrum as shown in FIG. 2, may allow determination of the laser 16 spectral shape rather than measuring the spectral shape of laser 16 from combined monitor-calibration beam 68. The determined shape can subsequently be deconvolved from the raw Raman spectrum. Substantially simultaneous spectral data collection in connection with integral transforms, in conjunction with the components of apparatus 10, combine to provide high resolution Raman spectra that are not dependent on frequency stability in source 12 of incident radiation 14, and are independent of intensity fluctuations associated with source of incident radiation 12. In addition, substantially simultaneous data measurements also allows user interchangeability of sample spectra among a number of spectrometers and similar apparatus because instrument variabilities are rendered irrelevant. Also, because corrections may be applied to correct for instrument variabilities, one or more multi-mode lasers not mode stabilized may be used as source 12 of incident radiation 14. As an additional result, more applications of the Raman principles are made possible, because a standard Raman spectrum is provided.

Collection of spectral data substantially simultaneously, and subsequent application of one or more integral transforms to the spectral data, in conjunction with the components of the apparatus of the present invention, contribute to providing high resolution Raman spectra that are not dependent on excitation frequency stability, and are independent of intensity fluctuations associated with source 12 of incident radiation 14. In addition, substantially simultaneous data measurements allow interchangeability of sample spectra among a number of spectrometers and similar instruments because instrument variabilities are rendered irrelevant.

Figure 3:
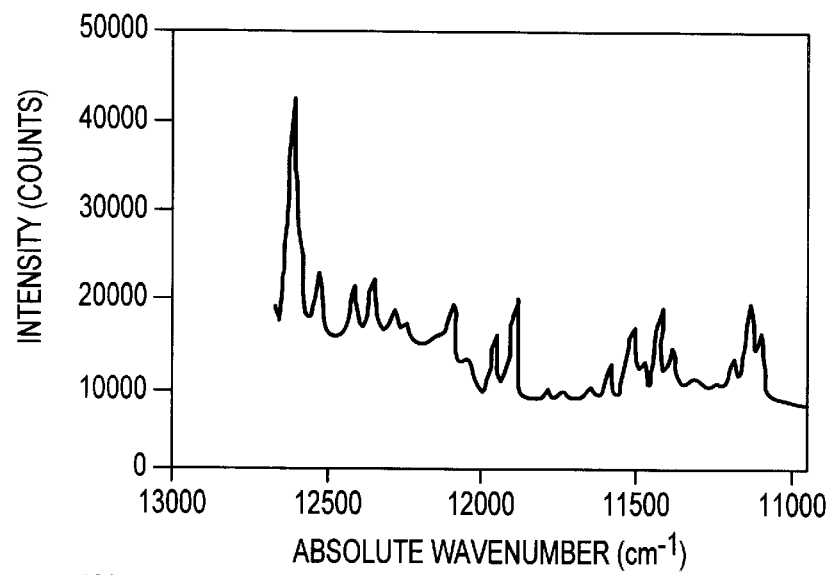
FIG. 3 is a graph showing spectral data associated with an incident beam obtained substantially simultaneously with the monitor beam data shown in FIG. 4.
Figure 4:
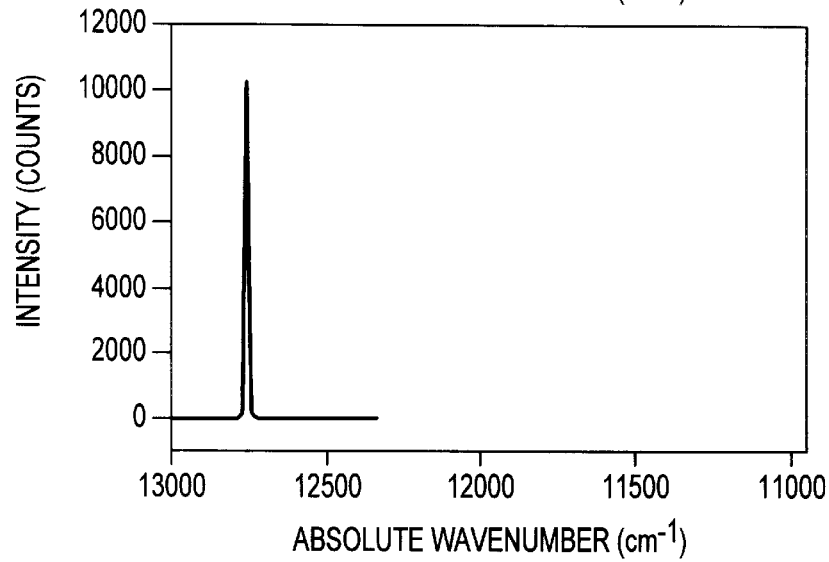
FIG. 4 is a graph showing spectral data associated with a monitor beam obtained substantially simultaneously with the data shown in FIG. 3.
Figure 5:
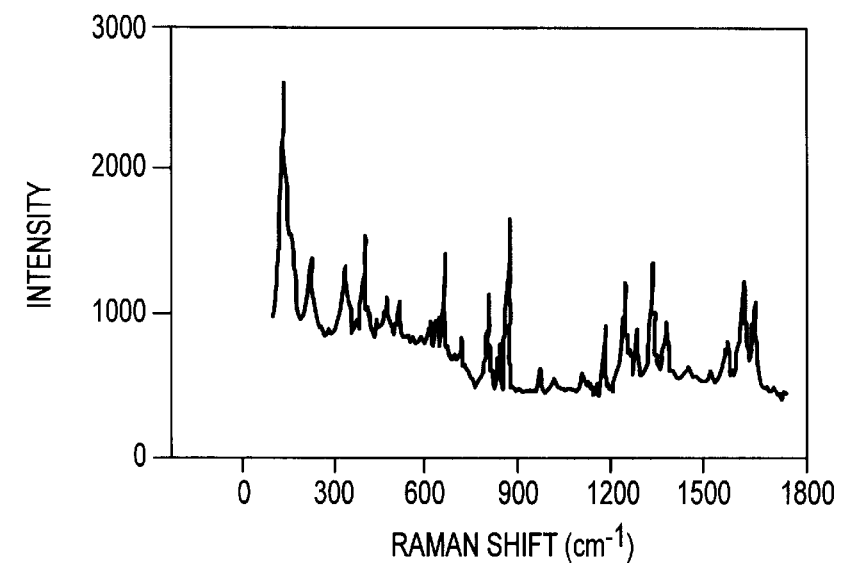
FIG. 5 is a graph showing spectral data associated with the Raman shift by application of one or more integral transforms to the spectral data obtained in accordance with the present invention.

Referring now by cross-reference among FIGS. 2–5, spectral data in connection with the present invention are provided. Shape correction for the resulting spectral data is shown and displayed as shown in FIG. 2. In addition, frequency calibration of the instrument may be displayed on a spatial channel as shown in FIG. 2. FIG. 2 includes a graph showing an array of spectral data obtained from a source of incident radiation in accordance with the present invention. FIG. 3 is a graph showing Raman spectral data associated with sample 26 obtained substantially simultaneously with the monitor beam spectral data shown in FIG. 4. FIG. 5 is a graph showing spectral data associated with the Raman shift by application of one or more integral transforms to the spectral data obtained in accordance with the present invention.

While the particular apparatus for measuring and applying instrumentation correction to produce a standard Raman spectrum as shown and disclosed in detail in this instrument is fully capable of obtaining the objects and providing the advantages stated, this disclosure is merely illustrative of the presently preferred embodiments of the invention, and no limitations are intended in connection with the details of construction, design or composition other than as provided and described in the appended

What is claimed is:

1. An apparatus for measuring and applying instrumentation correction to produce a standard Raman spectrum of a sample, comprising:
   a source of incident radiation;
   a waveguide for providing from the incident radiation an incident beam and a monitor beam;
   means for directing the incident beam to the sample;
   means for obtaining Raman radiation from the sample;
   a spectrometer for collecting spectral data from the Raman radiation and from the monitor beam; and
   means for determining from the Raman radiation and the monitor beam the standard Raman spectrum of the sample by application of one or more integral transforms to the spectral data.

2. An apparatus for measuring and applying instrumentation correction to produce a standard Raman spectrum of a sample as recited in claim 1, wherein the source of incident radiation is substantially monochromatic.

3. An apparatus for measuring and applying instrumentation correction to produce a standard Raman spectrum of a sample as recited in claim 2, wherein the source of incident radiation is a laser.

4. An apparatus for measuring and applying instrumentation correction to produce a standard Raman spectrum of a sample as recited in claim 1, wherein the standard Raman spectrum determining means includes means for collecting spectral data directly from the monitor beam and directly from the Raman radiation beam.

5. An apparatus for measuring and applying instrumentation correction to produce a standard Raman spectrum of a sample as recited in claim 4, wherein the standard Raman spectrum determining means includes means for collecting spectral data substantially simultaneously from the monitor beam and from the Raman radiation beam.

6. An apparatus for measuring and applying instrumentation correction to produce a standard Raman spectrum of a sample as recited in claim 1, wherein the standard Raman spectrum determining means further includes an intensity filter located in the path of the monitor beam for reducing intensity of the monitor beam.

7. An apparatus for measuring and applying instrumentation correction to produce a standard Raman spectrum of a sample as recited in claim 1, wherein the standard Raman spectrum determining means includes means for imparting to the monitor beam a frequency calibration standard for producing a combined monitor-calibration beam.

8. An apparatus for measuring and applying instrumentation correction to produce a standard Raman spectrum of a sample as recited in claim 7, wherein the standard Raman spectrum determining means includes means for imparting substantially simultaneously to the monitor beam a frequency calibration standard for producing a combined monitor-calibration beam.

9. An apparatus for measuring and applying instrumentation correction to produce a standard Raman spectrum of a sample as recited in claim 7, wherein the standard Raman spectrum determining means includes means for imparting sequentially to the monitor beam a frequency calibration standard for producing a combined monitor-calibration beam.

10. An apparatus for measuring and applying instrumentation correction to produce a standard Raman spectrum of a sample as recited in claim 7, wherein the standard Raman spectrum determining means includes a fiber optic waveguide located in the path of the combined monitor-calibration beam.

11. An apparatus for measuring and applying instrumentation correction to produce a standard Raman spectrum of a sample as recited in claim 7, wherein the standard Raman spectrum determining means includes a turning mirror for turning the combined monitor-calibration beam toward one or more dispersive gratings.

12. An apparatus for measuring and applying instrumentation correction to produce a standard Raman spectrum of a sample as recited in claim 1, wherein the standard Raman spectrum determining means includes means for applying a frequency calibration standard to the Raman radiation.

13. An apparatus for measuring and applying instrumentation correction to produce a standard Raman spectrum of a sample as recited in claim 12, wherein the standard Raman spectrum determining means includes means for applying a frequency calibration standard to the Raman radiation substantially simultaneously.

14. An apparatus for measuring and applying instrumentation correction to produce a standard Raman spectrum of a sample as recited in claim 12, wherein the standard Raman spectrum determining means includes means for applying a frequency calibration standard to the Raman radiation sequentially.

15. An apparatus for measuring and applying instrumentation correction to produce a standard Raman spectrum of a sample as recited in claim 1, wherein the standard Raman spectrum determining means includes means for applying shape correction to the Raman radiation.

16. An apparatus for measuring and applying instrumentation correction to produce a standard Raman spectrum of a sample as recited in claim 15, wherein the standard Raman spectrum determining means includes means for applying shape correction to the Raman radiation substantially simultaneously.

17. An apparatus for measuring and applying instrumentation correction to produce a standard Raman spectrum of a sample as recited in claim 15, wherein the standard Raman spectrum determining means includes means for applying shape correction to the Raman radiation sequentially.

18. An apparatus for measuring and applying instrumentation correction to produce a standard Raman spectrum of a sample as recited in claim 1, wherein the standard Raman spectrum determining means includes a detector.

19. An apparatus for measuring and applying instrumentation correction to produce a standard Raman spectrum of a sample, comprising:
   a source of incident radiation;
   means for providing from the incident radiation an incident beam and a monitor beam;
   means for directing the incident beam at the sample;
   means for generating from the sample a Raman beam;
   means for collecting spectral data directly from the monitor beam and directly from the Raman beam; and
   means for applying one or more integral transforms to the monitor beam spectral data and the Raman beam spectral data to produce the standard Raman spectrum of the sample.

20. An apparatus for measuring and applying instrumentation correction to produce a standard Raman spectrum of a sample as recited in claim 19, wherein the spectral data collecting means occurs substantially simultaneously.

21. An apparatus for measuring and applying instrumentation correction to produce a standard Raman spectrum of a sample as recited in claim 19, wherein the source of incident radiation is substantially monochromatic.

22. An apparatus for measuring and applying instrumentation correction to produce a standard Raman spectrum of a sample as recited in claim 21, wherein the source of incident radiation is a laser.

23. An apparatus for measuring and applying instrumentation correction to produce a standard Raman spectrum of a sample as recited in claim 19, wherein the incident beam and monitor beam providing means is a waveguide.

24. An apparatus for measuring and applying instrumentation correction to produce a standard Raman spectrum of a sample as recited in claim 23, wherein the incident beam and monitor beam providing means is a beam splitter waveguide.

25. An apparatus for measuring and applying instrumentation correction to produce a standard Raman spectrum of a sample as recited in claim 19, wherein the spectral data collecting means includes a spectrometer.

26. An apparatus for measuring and applying instrumentation correction to produce a standard Raman spectrum of a sample as recited in claim 25, wherein the spectral data collecting means includes one or more spectrometers.

27. An apparatus for measuring and applying instrumentation correction to produce a standard Raman spectrum of a sample as recited in claim 19, wherein the spectral data collecting means includes an interferometer.

28. An apparatus for measuring and applying instrumentation correction to produce a standard Raman spectrum of a sample as recited in claim 19, wherein the monitor beam spectral data collecting means includes means for imparting to the monitor beam a frequency calibration standard.

29. An apparatus for measuring and applying instrumentation correction to produce a standard Raman spectrum of a sample as recited in claim 28, wherein the monitor beam spectral data collecting means includes means for imparting to the monitor beam a frequency calibration standard substantially simultaneously.

30. An apparatus for measuring and applying instrumentation correction to produce a standard Raman spectrum of a sample as recited in claim 28, wherein the monitor beam spectral data collecting means includes means for imparting to the monitor beam a frequency calibration standard sequentially.

31. An apparatus for measuring and applying instrumentation correction to produce a standard Raman spectrum of a sample as recited in claim 19, wherein the monitor beam spectral data collecting means includes one or more fiber optic waveguides located in the path of the monitor beam.

32. An apparatus for measuring and applying instrumentation correction to produce a standard Raman spectrum of a sample as recited in claim 19, wherein the monitor beam spectral data obtaining means includes a plurality of dispersive apparatus for providing spectral resolution to the monitor beam.

33. An apparatus for measuring and applying instrumentation correction to produce a standard Raman spectrum of a sample as recited in claim 19, wherein the monitor beam spectral data obtaining means includes a plurality of higher order dispersive apparatus for providing higher spectral resolution to the monitor beam.

34. An apparatus for measuring and applying instrumentation correction to produce a standard Raman spectrum of a sample as recited in claim 19, wherein the Raman beam spectral data collecting means includes one or more sources of white light for imparting shape correction to the Raman beam.

35. An apparatus for measuring and applying instrumentation correction to produce a standard Raman spectrum of a sample as recited in claim 34, wherein the Raman beam spectral data collecting means includes one or more sources of white light for imparting shape correction to the Raman beam substantially simultaneously.

36. An apparatus for measuring and applying instrumentation correction to produce a standard Raman spectrum of a sample as recited in claim 19, wherein the Raman beam spectral data collecting means includes one or more sources of white light for imparting shape correction to the Raman beam sequentially.

37. An apparatus for measuring and applying instrumentation correction to produce a standard Raman spectrum of a sample as recited in claim 19, wherein the Raman beam spectral data collecting means includes means for adding a frequency calibration standard to the Raman beam.

38. An apparatus for measuring and applying instrumentation correction to produce a standard Raman spectrum of a sample as recited in claim 37, wherein the Raman beam spectral data collecting means includes means for adding a frequency calibration standard to the Raman beam substantially simultaneously.

39. An apparatus for measuring and applying instrumentation correction to produce a standard Raman spectrum of a sample as recited in claim 37, wherein the Raman beam spectral data collecting means includes means for adding a frequency calibration standard to the Raman beam sequentially.

40. An apparatus for measuring and applying instrumentation correction to produce a standard Raman spectrum of a sample as recited in claim 19, wherein the spectral data collecting means includes one or more multichannel detectors.

41. A method for manufacturing an apparatus for measuring and applying instrumentation correction to produce a standard Raman spectrum of a sample, comprising the steps of:

selecting a source of incident radiation;
  locating in the path of incident radiation means for providing from the incident radiation an incident beam and a monitor beam;
  including means for directing the incident beam at the sample and for generating a Raman beam;
  installing means for collecting monitor beam spectral data;
  providing means for collecting Raman beam spectral data and monitor beam spectral data substantially simultaneously; and
  equipping the apparatus with means for applying one or more integral transforms to the Raman beam spectral data and to the monitor beam spectral data to produce the standard Raman spectrum of the sample.

42. A method for manufacturing an apparatus for measuring and applying instrumentation correction to produce a standard Raman spectrum of a sample as recited in claim 41, wherein the selecting step includes the substep of selecting a source of substantially monochromatic light.

43. A method for manufacturing an apparatus for measuring and applying instrumentation correction to produce a standard Raman spectrum of a sample as recited in claim 41, wherein the locating step includes the substep of locating in the path of the incident radiation one or more waveguides.

44. A method for manufacturing an apparatus for measuring and applying instrumentation correction to produce a standard Raman spectrum of a sample as recited in claim 41, wherein the installing step includes the substeps of:

1. locating an intensity filter located in the path of the monitor beam for reducing intensity of the monitor beam;
  2. imparting to the monitor beam a frequency calibration standard for producing a combined monitor-calibration beam;
  3. placing a fiber optic waveguide located in the path of the monitor-calibration beam; and
  4. including a turning mirror for turning the monitor-calibration beam toward one or more dispersive gratings.

45. A method for manufacturing an apparatus for measuring and applying instrumentation correction to produce a standard Raman spectrum of a sample as recited in claim 41, wherein the providing step includes the substeps of:

a. installing means for applying a frequency calibration standard to the Raman beam; and
  b. including means for applying shape correction to the Raman beam.

* * * * *